United States Patent
Pietrabissa et al.

(10) Patent No.: US 7,399,309 B2
(45) Date of Patent: Jul. 15, 2008

(54) AUXILIARY FORCEPS FOR HAND-ASSISTED LAPAROSCOPIC SURGERY (HALS)

(75) Inventors: Andrea Pietrabissa, Pisa (IT); Cesare Stefanini, Cascina (IT); Arianna Menciassi, Pontedera (IT); Paolo Dario, Livorno (IT)

(73) Assignee: Scuola Superiore di Studi Universitari e di Perfezionamento S. ANNA, Pisa (IT)

( * ) Notice: Subject to any disclaimer, the term of this patent is extended or adjusted under 35 U.S.C. 154(b) by 579 days.

(21) Appl. No.: 10/480,881

(22) PCT Filed: Jun. 12, 2001

(86) PCT No.: PCT/IT01/00298

§ 371 (c)(1),
(2), (4) Date: Dec. 12, 2003

(87) PCT Pub. No.: WO02/100281

PCT Pub. Date: Dec. 19, 2002

(65) Prior Publication Data

US 2004/0153121 A1    Aug. 5, 2004

(51) Int. Cl.
*A61B 17/28* (2006.01)
(52) U.S. Cl. .................. 606/205; 81/300; 433/159
(58) Field of Classification Search ........ 606/205–207, 606/210, 133; 81/3.8, 489, 487, 490, 420, 81/427.5, 177.6; 294/99.2; D28/55; 224/219, 224/220, 267; 30/155, 255
See application file for complete search history.

(56) References Cited

U.S. PATENT DOCUMENTS

| | | | |
|---|---|---|---|
| 2,478,595 A | 8/1949 | Richter | |
| D253,974 S * | 1/1980 | Nalbandian | D28/55 |
| 5,062,173 A * | 11/1991 | Collins et al. | 7/118 |
| 5,590,971 A * | 1/1997 | Melnick | 401/202 |
| 5,743,450 A * | 4/1998 | Plate | 224/220 |
| 5,921,990 A * | 7/1999 | Webb | 606/110 |
| 6,149,642 A | 11/2000 | Gerhart et al. | 606/1 |
| 6,159,200 A | 12/2000 | Verdura et al. | 606/1 |
| 6,174,321 B1 | 1/2001 | Webb | 606/210 |

FOREIGN PATENT DOCUMENTS

| | | |
|---|---|---|
| DE | 3722311 A1 | 1/1989 |
| WO | 9800069 A | 1/1998 |
| WO | WO 0032117 | 6/2000 |

* cited by examiner

*Primary Examiner*—Todd E. Manahan
*Assistant Examiner*—Ryan Severson
(74) *Attorney, Agent, or Firm*—Pollack, P.C.

(57) ABSTRACT

Auxiliary forceps are provided for video-assisted minimally-invasive surgery, such as hand-assisted laparoscopic surgery, the forceps being intended for operation by a surgeon's non-dominant hand inserted through an incision for entering a patient's natural body cavity. The forceps comprises a plurality of actuating plates hinged elastically to one another and having a size and shape suitable for operation when held by the tips of two fingers. The forceps also has a plurality of jaws extending from each actuating plate, and a member for temporarily connecting the forceps to the surgeon's hand so as to maintain the forceps at an adjustable distance from the hand of not greater than a predetermined value. In addition, a structure is provided for housing the jaws relatively close to one another, within which the jaws are engaged during operation when the forceps is not in use.

16 Claims, 4 Drawing Sheets

AUXILIARY FORCEPS FOR HAND-ASSISTED LAPAROSCOPIC SURGERY (HALS)

FIELD OF THE INVENTION

The present invention relates generally to precision instruments and, more particularly, to instruments for minimally invasive surgery.

BACKGROUND OF THE INVENTION

Traditional hand-assisted laparoscopic surgery (or HALS) combines conventional minimally-invasive laparoscopic surgical techniques with those of classical open field surgery. More specifically, by the laparoscopic approach, through application of trocars (generally speaking, three access points) for the introduction of instruments used during surgical intervention by a laparoscope (either of the optical fiber type or those equipped with a CCD camera), a surgeon can visually access and maneuver relevant inner portions of a patient's abdomen. The diameter of the incisions made is typically between about 5mm and about 25 mm. Through insufflation of an inert gas, a working space, known as a pneumaperitoneum, is then created in the abdomen. This enables the surgeon to operate readily, without hindrance due to a lack of adequate space. In addition, an incision about 5-7 cm long is made near the first access points or incisions, through which the surgeon may introduce his/her generally non-dominant hand into the patient's abdomen and perform support operations (such as tissue displacement, retraction of organs to be operated on, palpation, interaction with other instruments, etc.).

To prevent loss of pneumaperitoneum through the incision(s), several types of sealing devices have been developed. These devices are intended to be applied to an incision so as to allow passage of the surgeon's hand therethrough, while preventing gas from escaping. Currently available sealing devices are of several types, for instance, either those having an adhesive flange to be secured to the abdominal wall or devices of an inflatable type. A conventional sealing device of the inflatable type that is considered especially comfortable and easy to use is one having a substantially tubular inflatable sleeve, with a twisted inner cross section, for providing a seal against the surgeon's arm once her/his hand has been inserted through the sleeve. The device also has a pair of sealing rings for closing the innerside and the outerside of the abdominal wall corresponding to the incision.

Hand-assisted laparascopic surgery has been successfully applied to a wide range of surgical procedures for example gastric resection, gastric by-pass, transhiatal esophgectomy, pancreatic and hepatic surgery, nephrectomy, colorectal surgery, aortic aneurysm repairs, etc. The main advantages of this technique as compared to conventional laparascopic surgery is that the surgeon retains both (i) direct tactile sensation of traditional surgery, which is not provided by modern, remotely controlled instruments, and (ii) the hand-eye coordination lost previously when surgeons began perfoeming surgery through a monitor. Furthermore the presence of the surgeon's hand in the surgical field enables greater ease in, and atraumatic displacement of, the organs, an immediate control of potentially dangerous situations, and gives him/her the ability to perform blunt dissections. In addition, the facility provided by use of an assisting hand makes the surgeon's task easier to perform, thereby reducing the level of training and experience usually required to master laparoscopic surgery techniques.

However, in the course of hand-assisted laparoscopic surgery, situations often occur where the surgeon's dexterity is no longer adequate to perform extraordinarily precise operations such as fine dissections, vascular peduncula isolation, limphade-nectomy, etc. In conventional open field surgery, when tissue to be grasped is only a few millimeters in size such that the surgeon's finger tips can be ineffective, the use of forceps, which is generally operated by the surgeon's non-dominant hand, is not problematic. During minimally invasive procedures, on the other hand, such as hand-assisted laparoscopic surgery, the use of conventional surgical forceps has not been possible. This is because of their shape, incompatibility with the space available in the surgical field, and the manner in which this type of minimally invasive intervention is carried out, namely, a need to minimize the number of times the non-dominant hand is extracted from and re-inserted into the surgical field.

OBJECTS AND SUMMARY OF THE INVENTION

Accordingly, it is an object of the present invention to provide relatively small dimension, structurally simple, and reliable forceps for surgical use, which are not only suitable for general use by a surgeon, as necessary, but also for video-assisted, minimally invasive surgical procedures, in particular, hand assisted laparoscopic techniques.

Another object of the present invention is to provide forceps having a shape, dimensions and structure suitable to be kept at the surgeon's disposal for selected use in the patient's abdominal cavity during intervention and in such a position that it may be quickly and easily grasped using the surgeon's fingers, when necessary, or can be parked after use without risk of accidental damage to surrounding organs and tissue.

A further object of the present invention is to provide forceps adapted for positioning integral to a surgeon's hand upon use and, when not in use during intervention, may be parked in a patient's abdominal cavity without risk of its jaws posing a danger of lesions to surrounding body structures.

Still another object of the present invention is to provide forceps configured for operation by a minimum number of fingers (e.g., two).

Yet another object of the present invention is to provide a method of performing hand-assisted laparoscopic surgery, which is not only easier for the surgeon, but also allows operations to be accomplished that would otherwise be impossible to perform manually alone.

According to one aspect of the present invnetion, an auxiliary forceps is provided for video-assisted, minimally invasive surgery, such as hand-assisted laparoscopic surgery. The forceps preferably comprise a plurality of actuating plates, hinged elastically to one another and having a shape and dimensions such that they may be operated when kept between the tips of two fingers of a surgeon's hand, and by a plurality of jaws, each extending from a respective actuating plate. The forceps further provide for temporary connection to the surgeon's hand, for maintaining the forceps at an adjustable distance from the hand of not greater than a predetermined value, and for housing the jaws in a mutually side-by-side condition, within the housing structure, the jaws being engaged when, during intervention, the forceps are not in use.

In accordance with another aspect of the present invention, a forceps is provided that may be secured to a surgeon's hand by a cord joined to actuating plates. The forceps includes an anchoring device, such as a loop made from the same cord, and an elastic ring or a clamp that is adjustable in width and distance relative to the plates. Preferably, a housing of the jaws is formed either of a removable prtoective cap connected to the plates by a cord of adjustable length, or by a seat perimetrically formed at an edge of the plates. In the latter case, the jaws are of a retractable type - the jaws having a curved shape and an angular displacement from an operating position to a rest position within the seat.

BRIEF DESCRIPTION OF THE DRAWINGS

A specific, illustrative auxiliary forceps for video-assisted, minimally invasive surgery, according to the present invention, is described below with reference to the accompanying drawings, in which.

DETAILED DESCRIPTION OF THE PREFERRED EMBODIMENTS

Figure 1:
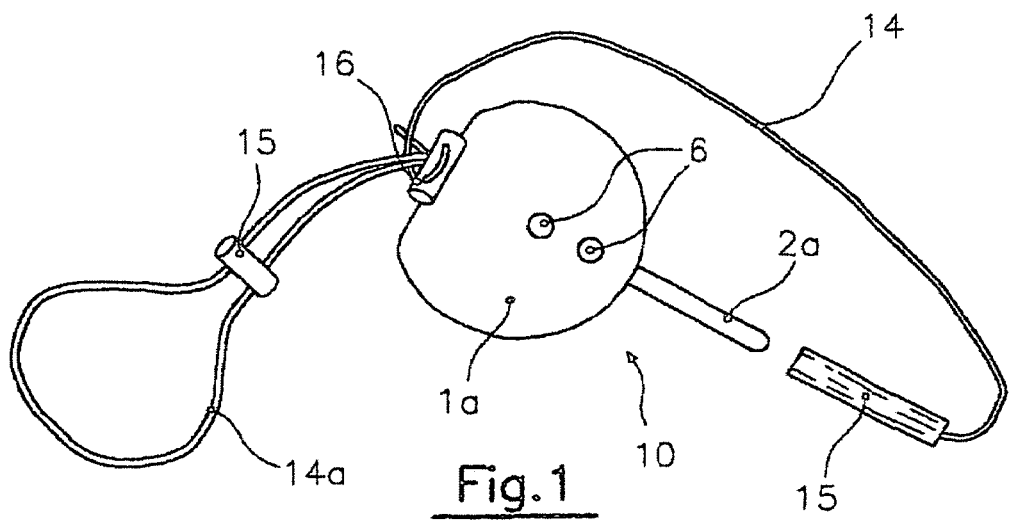
FIG. 1 is a plan view of an auxiliary forceps, according to one aspect of the present invention.

Referring now to the drawings and, more particularly, to FIGS. 1-8, there is shown generally a specific, illustrative auxiliary forceps for hand-assisted laparoscopic surgery, in accordance with various aspects of the present invention. According to one embodiment, shown generally in FIGS. 1, 2 and 3, a forceps 10 is provided, that preferably includes a pair of substantially circular actuating plates 1a, 1b joined to one another by a pin 3 extending at a chord thereof. Actuating plates 1a, 1b are very small, but sufficient in size to be grasped and actuated by-holding-them when held between the tips of two fingers such as of a surgeon's hand, which size corresponds to a few centimeters in diameter (for example, about 3 cm). Respective jaws 2a, 2b may be mounted securely to plates 1a, 1b in any suitable fashion, for example, as shown in the drawings, by screws 4, and extend from a portion diametrically opposed to pin 3 and perpendicularly thereto. The heads of screws 4 are desirably housed within respective seats 5 formed on plates 1a, 1b and concealed by covering caps 6 mounted suitably thereon such as by snap-fit reception. A spring 7, for example of a flat type, is interposed between plates 1a and 1b to keep jaws 2a, 2b in spaced apart relation relative to one another. A diametrical channel 9, extending from the perimetrical edge of plate 1a to the inner end of jaw 2a, is formed in plate 1a to connect jaw 2a through an electric cable to an electric power source, for instance, to enable the forceps to be used for unipolar or bipolar electrocoagulation.

A bracket 12 with through hole 13 extends from a facing 11 formed on a perimetrical edge of plate 1a (plate 1b having a corresponding facing), from the portion diametrically opposed to jaw 2a. A cord 14 is tied to hole 13 and a cap 15 is secured to cord 14 for acting as a sheath for jaws 2a, b of the forceps, when not in use. Cord 14 forms a loop 14a of adjustable width by sliding a cord-clamping slider 15. A second slider 16, engaged with cord 14 immediately dowstream of bracket 12, aids in adjusting the length of the cord at the end to which cap 15 is affixed. Equivalently, and as an alternative to loop 14a, cord 14 may be provided with an elastic ring or a securing clamp.

In use, forceps is desirably secured by loop 14a to a phalanx or the wrist of a surgeon's non-dominant hand, before inserting the hand in the abdomen, while jaws 2a, 2b are placed in cap 15. In this manner, any risk of lesions caused accidentlly to the surrounding tissues is avoided and, simultaneously, jaws 2a, 2b are maintained in relatively close proximity to one another, thus overcoming the bias of spring 7 and retaining forceps 10 in a closed position. When the forceps is to be used, the surgeon removes cap 15 and operates the forceps by holding the actuating plates between two finger tips. To make it easier for them to be grasped between his/her fingers, a surface of plates 1a, b may be worked or otherwise processed in various ways, such as by grooving, as in the present embodiment, or by ribbing, curling and/or the like.

When not in use, the forceps remains anchored to the surgeon's hand through cord 14 at a selected distance not greater than the length of the cord portion of the cord comprised between cord clamps 15 and 16, and then secured at such distance, as needed.

Alternatively or concurrently, protective cap 15 is replaced by a substantially C-shaped sheath (not shown) pivotally connected to one of the plates. Upon rotation in one direction, the sheath jaws may be engaged within the C-shaped sheath, or can be disengaged therefrom upon their rotation in another direction, thus achieving the same function as cap 15.

Figure 2:
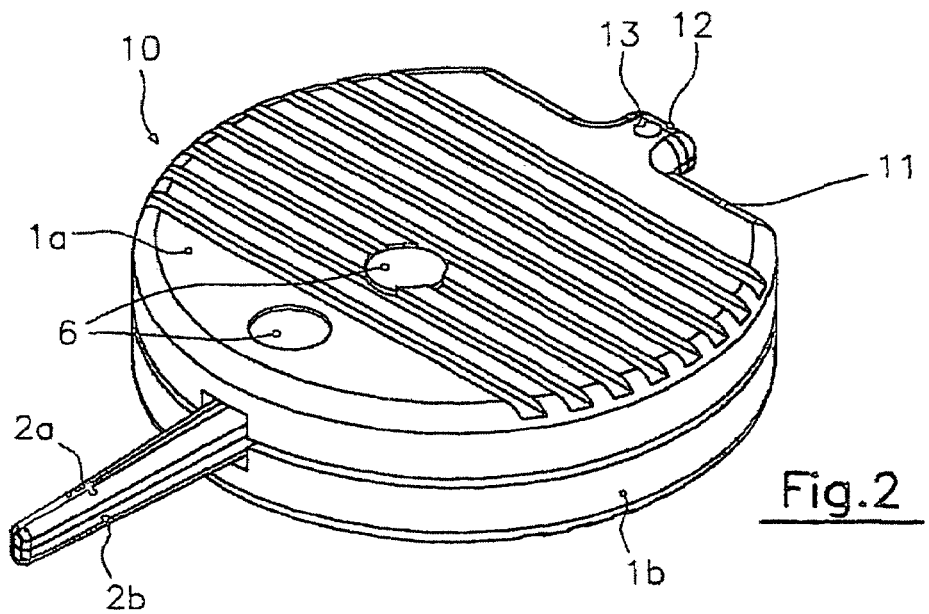
FIG. 2 is an enlarged perspective view of the forceps of FIG. 1.
Figure 3:
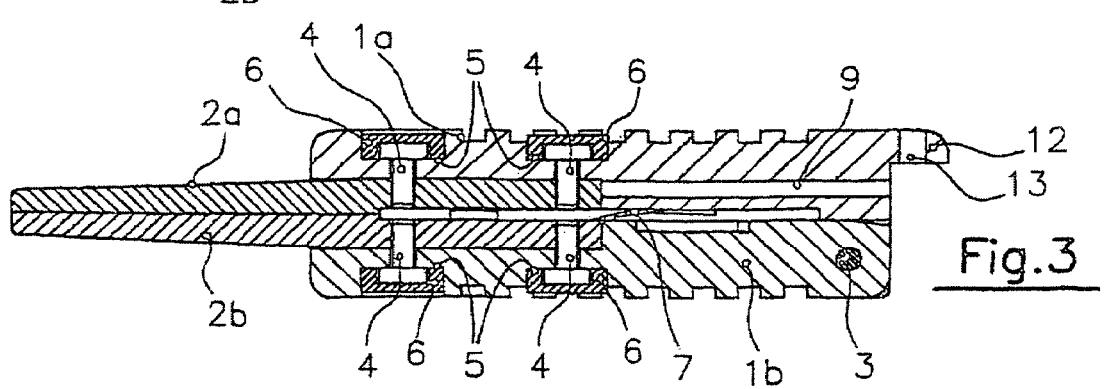
FIG. 3 shows a diametric section of the forceps of FIG. 2, taken along the axis of the forceps jaws.
Figure 4:
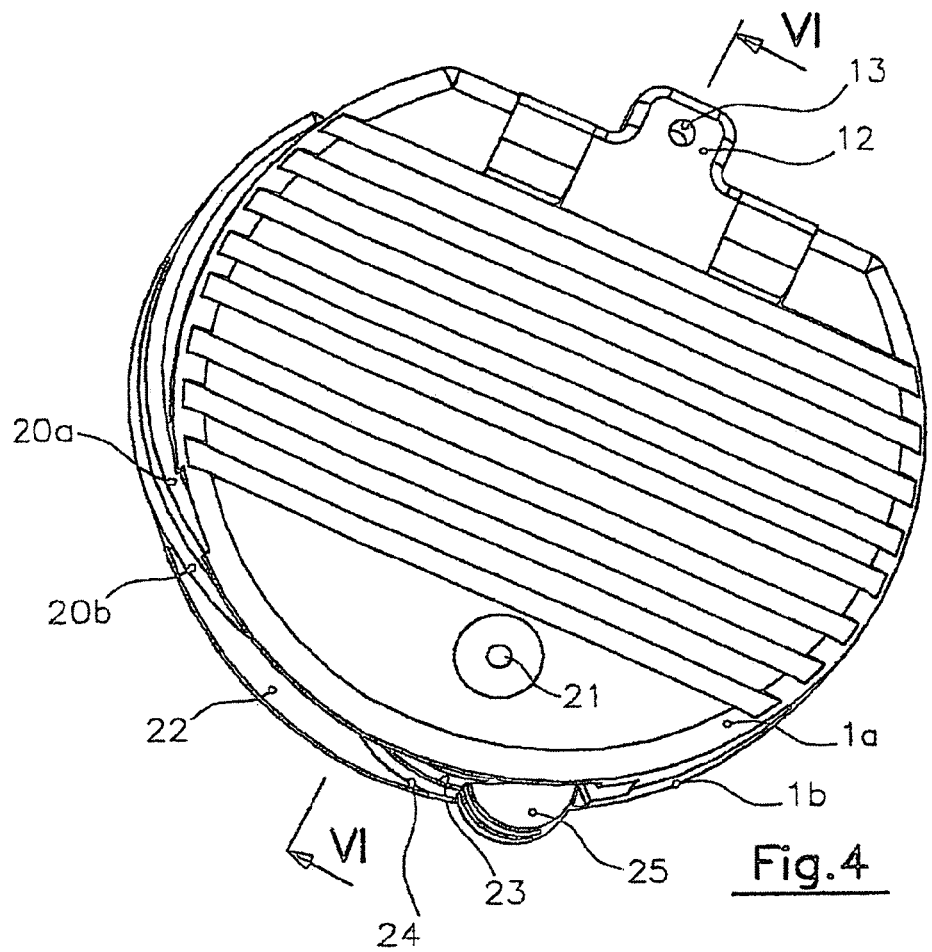
FIG. 4 is a perspective view of a forceps, in accordance with another aspect of the present invention, in a closed position.
Figure 5:
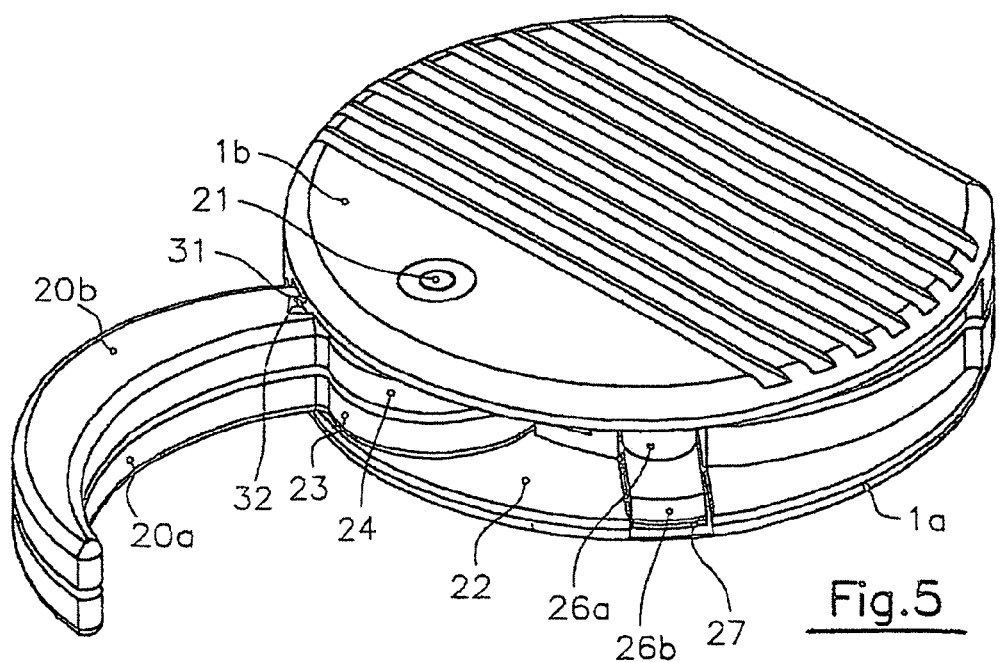
FIG. 5 is a perspective view of the forceps according to FIG. 4 in an open position.
Figure 6:
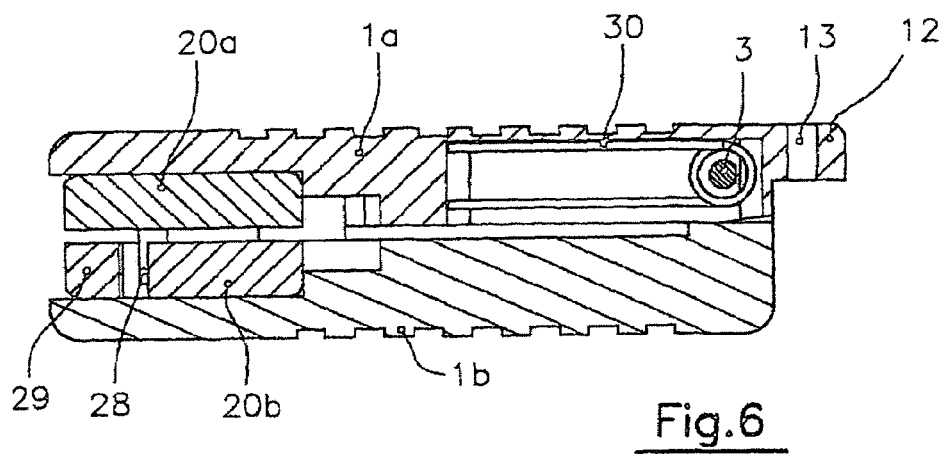
FIG. 6 is a sectional view taken along line VI-VI of FIG. 4.
Figure 7:
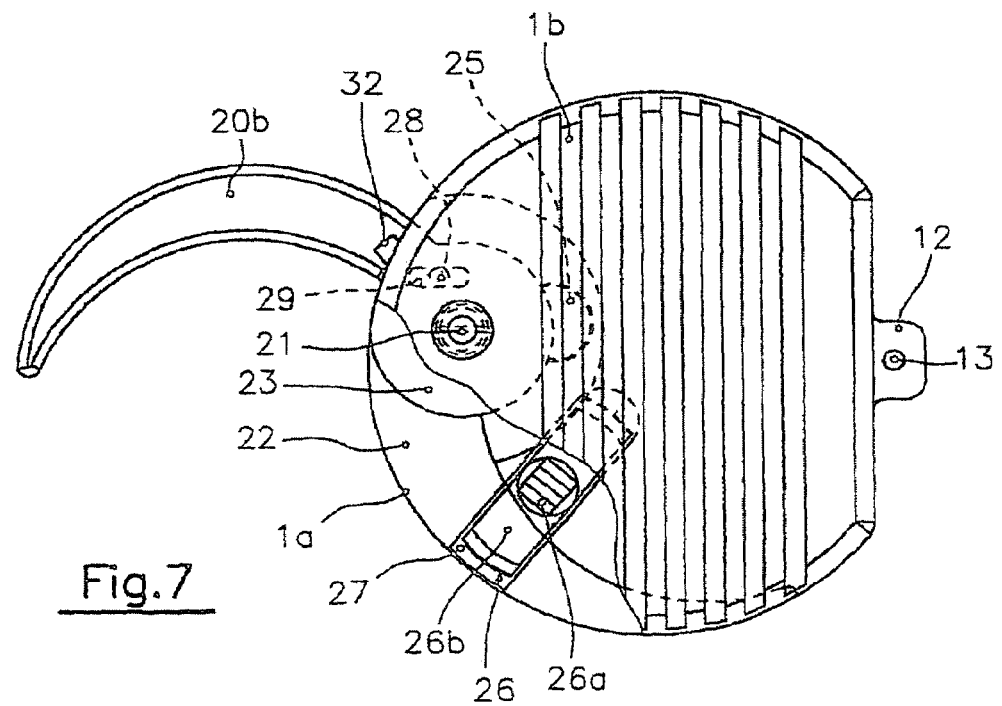
FIG. 7 is a partially sectioned, plan view of the forceps illustrated in FIG. 5.

In accordance with another aspect of the present invention, shown generally in FIGS. 4-7, jaws 20a and 20b are provided which are retractibly housable within a housing seat 22 formed on a perimetrical edge of actuating plates 1a and 1b; the same numerals being used to indicate the respective components as those used with the forceps in FIGS. 1-3. Consequently, jaws 20a 20b have a curved shape that extend from an enlarged portion, or root, 23, 24, respectively, from which they are hinged to actuating plates 1a, 1b by respective pins 21. Actuating plates 1a, 1b are hinged to one another through a pin 34, as before. An elastic member 30, for instance, as shown in FIG. 6, is provided therebetween to keep the forceps in an open position.

As best seen in FIG. 4, jaws 20a, 20b are formed at roots 23, 24, respectively, having a side protrusion 25 that allows a tangential force to be exerted on the roots, releasing jaws 20a, 20b and thus enabling them to achieve reach the operative or working position shown in FIG. 5.

To maintain the forceps in a closed position when the jaws are in a stowed or resting position, illustrated in FIG. 4, a fastening device is provided between the actuating plates. The device, according to one arrangement, is a substantially T-shaped bracket 26 affixed to one of the plates, e.g., plate 10b, by its leg 26a and extends with its transverse portion 26b within housing seat 22, in a groove 27 correspondingly formed in the other plate, e.g., plate 10a. In this manner, when jaws 20a, 20b are placed in the housing seat, the jaw integral to the plate, and within which groove 27 is formed, abuts on transverse portion 26b of the bracket, such that it cannot escape from the groove, thereby securing the plates to one another.

So that relatively precise mutual parallelism of jaws 20a 20b is achieved in any position, a pin 28 (see FIGS. 6 and 7) extends from one plate to the other and engages a slot 29 formed in the root of the latter plate. Slot 29 is so oriented as to be generally perpendicular to the forceps hinge when the jaws are in an operative position. Pin 28 may then tilt within slot 29 when the jaws are in spaced apart relation to one another, and keeps the jaws secured to one another when they are closed.

The force exterted on jaws 20a, 20b, while in the stowed or retracted position, by elastic member 30 through transverse portion 26b of bracket 26, normally keeps the forceps in the closed position it being necessary to slightly urge against protrusion 25 to open the forceps. To then maintain the jaws in the operative position, an end-stroke locking device is provided, such as a tooth 31 (shown in FIGS. 5 and 7), protruding from one of the plates towards the other and snap engaging within a cavity 32 formed correspondingly in the jaws integral to the same plate. Cavity 32 and/or tooth 31 can be formed with inclined walls or sides to make snap engagement/disengagement easier, while also taking advantage of the elasticity of the material. Although the present invention has been shown and described in connection with the above-described locking arrangement, use of other functionally equivalent, end-stroke locking devices, may be appreciated by those skilled in the art, based on a rearview this disclosure.

The forceps, according to the present invention, are advantageously in not requiring that the jaws be capped. This is because, when not in use, the jaws are housed retractably in seat 22, formed perimetrically on edges of plates 1a, 1b. To secure the forceps to a surgeon's hand, the same solution as is provided by the forceps of FIGS. 1-3 above may be used. Specifically, a cord 14 is tied to bracket 12 through hole 13, forming a loop 14a of a diameter which is adjustable by a cord clamp slider 15.

Figure 8:
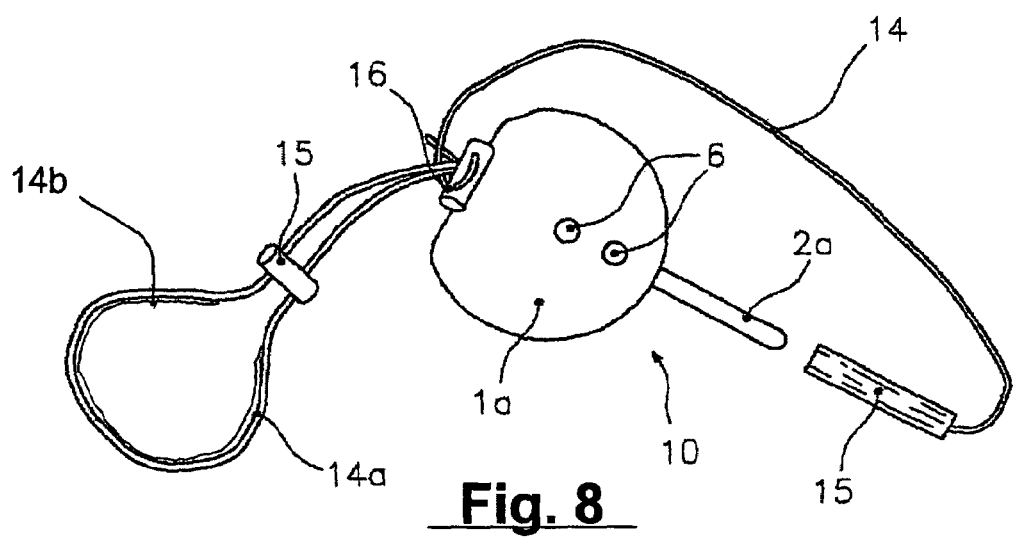
FIG. 8 is a plan view of an auxiliary forceps, according to another aspect of the present invention.

Another method of securing auxiliary forceps to the surgeon's hand, according to the present invention, is illustrated generally in FIG. 8. In particular, the forceps includes a cord-anchoring adhesive member 14b for application to the glove worn by the surgeon. The member is applied in such a position as to not hinder movement of the surgeon's hand, such as on the back of his/her hand, or at the base of a finger phalanx (like a ring or hemi-ring with an adhesive plate).

Facing surfaces of the jaws are shaped in a substantially conventional manner, according to the function they are intended to perform. For example, the jaw surfaces can be toothed for better grasping of the tissues and/or formed with a suitable seat for holding a needle, or with other shapes according to the function desired.

Overall, the auxiliary forceps, according to the present invention, has numerous advantages for hand-assisted laparoscopic surgery. First, it allows a number of different types of operations to be performed which could not otherwise be carried out without the help of a surgeon's hand (vascular peduncula isolation, lynphoglandula ablation, grasping of small portions of tissues). Second, the very small size of the forceps (operating plates 1a, 1b being a few centimeters in diameter) a minimizes interference, while still allowing relatively easy and firm handling of the forceps when the plates are grasped by two fingers. Third, they have a relatively wide actuating surface for the surgeon's fingers which makes a third fulcrum (e.g., the hollow at the thumb root), unnecessary, as is otherwise required by conventional, elongated structure forceps.

Moreover, their substantially circular shape, with streamlined and/or rounded off edges, makes them extremely safe to use, being nearly risk-free for causing accidental lesions to the tissues. Furthermore, with the forceps described above in which the jaws are curved, the shape of the jaws provides the benefit of minimizing hindrance or obstruction when the instrument is in a stowed or resting condition. This also allows the forceps to be used both for grasping and dissecting the tissues, with the possibility of surrounding vascular structures according to techniques well-known in the art.

Generally speaking, the forceps, according to the present invention, is intended for use as a disposable instrument. However, in the alternative, it may be constructed of one or more materials suitable for sterilization according to known techniques and, therefore, re-used. Preferably, the operating plates are either relatively dark in color or transparent, to avoid undesirable reflection which can disturb the surgeon's view of the surgical field through a monitor. The transparency also allows sight of the otherwise concealed portion of the surgical field to be maintained through the plates.

Various modifications and alterations to the invention may be appreciated based on a review of this disclosure. These changes and additions are intended to be within the scope and spirit of the invention as defined by the following claims.

What is claimed is:

1. Auxiliary forceps for minimally-invasive surgery, comprising:
   a plurality of actuating plates elastically hinged to one another and shaped and sized suitably for operation by and engagement with tips of a surgeon's fingers;
   a plurality of jaws, at least one jaw extending from each of the respective actuating plates;
   a connection member for temporarily connecting the forceps to the surgeon's hand and, thereby, maintaining the forceps at an adjustable distance from the hand of not greater than a predetermined value; and
   a structure for housing the jaws close to one another, within which the jaws are engaged when, during operation, the forceps is not in use;
   wherein the jaws are pivotally connected to the respective actuating plates and the housing structure comprises a seat formed along a perimetrical edge of the plates, the jaws having a correspondingly curved shape to be placed within the seat in a rest position following an angular displacement from an operating position, wherein the jaws extend in a substantially radial direction from the plates, the jaws being formed with a side protrusion through which a force for effecting the angular displacement from the rest position to the operating position is exerted.

2. The forceps set forth in claim 1, wherein the connection member comprises a cord connected to the actuating plates and having a connection device applied to a finger or wrist of the surgeon's non-dominant hand for adjusting its width and distance from the plates.

3. The forceps set forth in claim 2, wherein the connection device is a loop constructed of the same cord.

4. The forceps set forth in claim 2, wherein the connection device is an adhesive member, adapted to be applied to a surgeon's glove at such a position as to not hinder movement of the hand to which the cord is joined.

5. The forceps set forth in claim 1, wherein the jaws are relatively firmly connected to the respective actuating plates and the housing structure for the jaws comprises a removable protective cap connected to the plates through a cord of adjustable length.

6. The forceps set forth in claim 1, wherein a fastener is provided for keeping each of the actuating plates close to one another when the jaws are in their rest position.

7. The forceps set forth in claim 6, wherein the fastener comprises a bracket integral with one of the plates, extending toward the other plate, and having an arm arranged in a groove formed in the other plate of the housing seat for the jaws, whereby, when the jaws are engaged with the housing seat, the jaw integral with the plate, in which the groove for the arm is formed, abuts the arm integral with the other plate, thereby anchoring the plates to one another.

8. The forceps set forth in claim 1, wherein a slot is formed on one of the jaws in such a way as to be substantially orthogonal to the hinge axis of the actuating plates when the jaws are in the operating position, and a pin extends from the other jaw for engaging the slot to prevent relative sliding of the jaws when angularly displaced between the rest position and the operating position, while allowing them to spread apart during use.

9. The forceps set forth in claim 1, wherein reversible locking devices are provided for securing the jaws in the operating position and in the rest position, respectively.

10. The forceps set forth in claim 9, wherein the device for reversibly locking the jaws in the operating position comprises a cavity formed in at least one of the jaws and a tooth correspondingly extending from the respective actuating plate, for reversible snap engagement within the cavity when the jaws reach their operating position.

11. The forceps set forth in claim 9, wherein an elastic member is provided between the actuating plates for keeping them spread apart and urging the arm of the bracket against the jaws to reversibly fasten them in the rest position.

12. The forceps set forth in claim 1, wherein the housing structure comprises a sheath connected to one of the plates and turnable to cover the jaws following an angular displacement when the forceps is not in use.

13. The forceps set forth in claim 1, wherein the actuating plates are made of transparent or dark colored material.

14. The forceps set forth in claim 1, wherein the actuating plates have a substantially circular shape and rounded edges.

15. A method for performing intervention by minimally-invasive surgery in which a surgeon's hand is inserted into an operative field through an incision near incisions where trocars are engaged, the method comprising the steps of:
associating an auxiliary forceps with the hand; and
making the forceps integral with the hand at the time of intervention through a temporary connection member for adjustably maintaining the forceps a selected distance from the hand of not greater than a predetermined value, the forceps comprising a plurality of actuating plates elastically hinged to one another and having a shape and size for enabling them to be actuated by and engaged with tips of the surgeon's fingers, a plurality of jaws extending from the plates, and a structure for housing the jaws, integral with the plates, when the forceps is not in use, the jaws being released from the housing structure through sliding movement or angular displacement applied by the surgeon when the forceps is used, the jaws being pivotally connected to the respective actuating plates and the housing structure comprising a seat formed along a perimetrical edge of the plates, the jaws also having a correspondingly curved shape to be placed within the seat in a rest position following an angular displacement from an operating position, wherein the jaws extend in a substantially radial direction from the plates, the jaws being formed with a side protrusion through which a force for effecting the angular displacement from the rest position to the operating position is exerted.

16. The method set forth in claim 15, wherein the connecting member comprises a cord joined to the actuating plates and having a connection device applied to a finger or wrist of the surgeon's non-dominant hand for adjusting its width and distance from the plates.

* * * * *